United States Patent [19]

Henkelmann et al.

[11] Patent Number: 5,296,614
[45] Date of Patent: Mar. 22, 1994

[54] PREPARATION OF PHTHALIDES

[75] Inventors: Jochem Henkelmann; Thomas Ruehl, both of Ludwigshafen; Horst Zimmermann, Mannheim, all of Fed. Rep. of Germany

[73] Assignee: BASF Aktiengesellschaft, Ludwigshafen, Fed. Rep. of Germany

[21] Appl. No.: 969,725

[22] Filed: Oct. 30, 1992

[30] Foreign Application Priority Data

Nov. 11, 1991 [DE] Fed. Rep. of Germany ....... 4136992

[51] Int. Cl.$^5$ ........................................... C07D 307/87
[52] U.S. Cl. ..................................... 549/307; 549/310
[58] Field of Search ................................ 549/307, 310

[56] References Cited

U.S. PATENT DOCUMENTS

| | | | |
|---|---|---|---|
| 3,957,825 | 5/1976 | Urry et al. | 549/270 |
| 4,178,295 | 12/1979 | Englaender et al. | 549/307 |
| 4,485,246 | 11/1984 | Lyons | 549/302 |
| 4,528,385 | 7/1985 | aus der Fünten et al. | 549/307 |
| 4,973,713 | 11/1990 | Manogue | 549/307 |
| 5,100,456 | 3/1992 | Tsantrizos et al. | 549/310 |

FOREIGN PATENT DOCUMENTS

| | | |
|---|---|---|
| 2803319 | 8/1979 | Fed. Rep. of Germany . |
| 3201300 | 7/1983 | Fed. Rep. of Germany . |
| 0184683 | 7/1990 | Japan . |

Primary Examiner—C. Warren Ivy
Assistant Examiner—A. Owens
Attorney, Agent, or Firm—John H. Shurtleff

[57] ABSTRACT

A process for the preparation of phthalides of the formula I

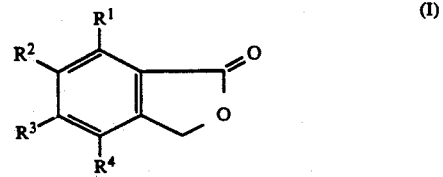

where $R^1$, $R^2$, $R^3$ and $R^4$ independently of one another, are hydrogen, $C_1$- to $C_4$-alkyl or $C_1$- to $C_4$-alkoxy, by reacting phthalic anhydrides of the formula II

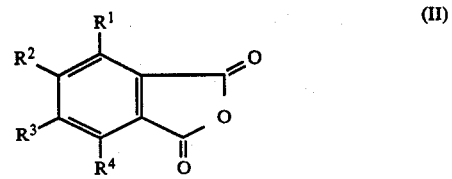

where $R^1$, $R^2$, $R^3$ and $R^4$ are as defined as above, on hydrogenation catalysts at from 50° to 400° C. and at from 1 to 400 bar, wherein the hydrogenation catalysts employed are essentially free from Lewis acids.

16 Claims, No Drawings

PREPARATION OF PHTHALIDES

The present invention relates to a process for the preparation of phthalides by catalytically hydrogenating phthalic anhydrides on fixed-bed catalysts which are essentially free from Lewis acids.

U.S. Pat. No. 4,485,246 and U.S. Pat. No. 3,957,825 disclose that phthalide can be prepared from phthalic anhydride by hydrogenation using homogeneous ruthenium catalysts.

DE-A-32 01 300 discloses the catalytic hydrogenation of phthalic anhydride using nickel as catalyst and methyl benzoate as solvent.

U.S. Pat. No. 4,973,713 discloses a process in which phthalic anhydride is hydrogenated batchwise on palladium/rhenium catalysts with addition of iron chloride.

The hydrogenation catalysts used hitherto have been employed as suspension or homogeneous catalysts, which are difficult to remove during work-up.

It is an object of the present invention to overcome the abovementioned disadvantages.

We have found that this object is achieved by a novel and improved process for the preparation of phthalides of the formula I

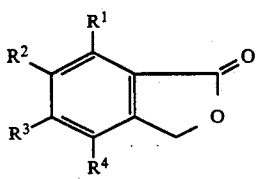

where $R^1$, $R^2$, $R^3$ and $R^4$, independently of one another, are hydrogen, $C_1$- to $C_4$-alkyl or $C_1$- to $C_4$-alkoxy, by reacting phthalic anhydrides of the formula II

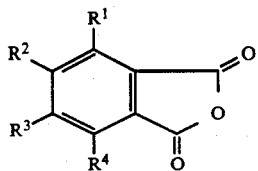

where $R^1$, $R^2$, $R^3$ and $R^4$ are as defined above, on hydrogenation catalysts at from 50° to 400°0 C. and at from 1 to 400 bar, where the hydrogenation catalysts employed are fixed-bed catalysts which are essentially free from Lewis acids.

The novel catalytic hydrogenation can be carried out as follows:

The phthalic anhydride II, the hydrogenation catalyst and if desired an inert solvent are introduced into a pressure reactor, the starting mixture is heated, and, if necessary, hydrogen is injected.

Alternatively, the hydrogenation catalyst can be in the form of a fixed bed in a tubular reactor, and the phthalic anhydride II, if desired dissolved in an inert solvent, is passed upward or downward through the reactor together with the hydrogen.

In addition to the anhydrides themselves, it is also possible to employ the corresponding dicarboxylic acids, monoesters and diesters, or mixtures thereof. All these starting materials can be introduced into the process according to the invention in solid, liquid or gaseous form. Phthalic anhydride is particularly preferred.

The hydrogenation can be carried out at from 50° to 400° C., preferably at from 150° to 250° C., and at from 1 to 400 bar, preferably at from 50 to 400 bar, particularly preferably at from 100 to 300 bar. However, the reaction temperature is highly dependent on the type of catalyst used.

The reaction can be carried out batchwise, but is preferably carried out continuously, with upward or downward flow over the catalyst, which is fixed in location, for example in the form of a fixed-bed catalyst. A weight hourly space velocity of from 0.01 to 1 kg, in particular from 0.05 to 0.4 kg, of phthalic anhydride II per liter of catalyst and per hour has proven successful.

Examples of reactors which can be used are tubular reactors and tube-bundle reactors.

Suitable hydrogenation catalysts are preferably oxides from main groups one to four of the Periodic Table of the Elements, such as lithium, sodium, potassium, calcium, boron, aluminum, silicon and tin, preferably tin, boron and aluminum, preferably tin and boron, sub-groups one to eight of the Periodic Table of Elements such as titanium, zirconium, vanadium, niobium, chromium, molybdenum, manganese, rhenium, cobalt, nickel, ruthenium, rhodium, palladium, osmium, iridium, platinum, copper and silver, preferably cobalt, ruthenium, palladium, copper and silver, particularly preferably palladium, copper and silver, or the lanthanide group, such as lanthanum, praseodymium, samarium and ytterbium, preferably praseodymium, or mixtures thereof.

Also suitable are metallic catalysts on support materials. Suitable metals are ruthenium, rhenium, palladium, platinum, boron and tin, preferably palladium, rhenium, ruthenium, tin and boron, particularly preferably palladium and rhenium.

The hydrogenation catalysts contain, for example, from 0 to 70% by weight, preferably from 15 to 60% by weight, of CuO, from 0 to 99% by weight, preferably from 50 to 99% by weight of CoO, from 0 to 70% by weight, preferably from 20 to 60% by weight, of NiO, from 0 to 50% by weight, preferably from 5 to 30% by weight, of $ZrO_2$, from 0 to 70% by weight, preferably from 30 to 70% by weight, of $Cr_2O_3$, from 0 to 99% by weight, preferably from 40 to 99% by weight, of $Al_2O_3$, from 0 to 99% by weight, preferably from 50 to 90% by weight, of $SiO_2$, from 0 to 99% by weight, preferably from 80 to 99% by weight, of carbon, for example as activated charcoal, from 0 to 20% by weight, preferably from 1 to 15% by weight of MoO, from 0 to 20% by weight, preferably from 1 to 10% by weight, of $MnO_2$, from 0 to 10% by weight, preferably from 1 to 7% by weight of $PrO_2$, from 0 to 20% by weight, preferably from 1 to 15% by weight, of AgO, from 0 to 30% by weight, preferably from 0.1 to 20% by weight, of $Na_2O$, from 0 to 10% by weight, preferably from 0.1 to 10% by weight, of PdO, from 0 to 10% by weight, preferably from 0.1 to 5% by weight, of Ru, from 0 to 10% by weight, preferably from 0.1 to 10% by weight, of Re, from 0 to 10% by weight, preferably from 0.1 to 10% by weight, of Pd, from 0 to 10% by weight, preferably from 0.5 to 5% by weight, of Sn, and from 0 to 10% by weight, preferably from 0.1 to 5% by weight, of B.

The catalysts may be employed either as supported catalysts or in compact form, ie. without supports. The percentages by weight with the support materials add up-. to 100% by weight.

The support materials used can be conventional materials, for example pumice, silicon dioxide, aluminum oxide, titanium dioxide, activated charcoal, silicates and zeolites, preferably activated charcoal, aluminum oxide, silicon dioxide and titanium dioxide, particularly preferably activated charcoal, aluminum oxide and silicon dioxide.

If necessary, the catalysts can be prepared in the presence of binders or molding assistants, such as sodium carbonate, potassium carbonate, sodium oxide and magnesium oxide, preferably sodium oxide.

Examples of suitable inert solvents are ethers, such as diethyl ether and tetrahydrofuran, preferably tetrahydrofuran, esters, such as ethyl acetate and methyl benzoate, lactones, such as butyrolactone, preferably butyrolactone, alcohols such as ethanol, butanol and propanol, preferably butanol, and water. Preferred groups of solvent are ethers, esters and lactones.

Work-up is by conventional methods, such as distillation.

The substituents $R^1$, $R^2$, $R^3$ and $R^4$ in the compounds I and II are defined as follows:
independently of one another
hydrogen,
$C_1$- to $C_4$-alkyl, such as methyl, ethyl, n-propyl, isopropyl, n-butyl, isobutyl, sec-butyl and tertbutyl, preferably methyl and ethyl, particularly preferably methyl,
$C_1$- to $C_4$-alkoxy, such as methoxy, ethoxy, n-propoxy, isopropoxy, n-butoxy, isobutoxy, sec-butoxy and tert-butoxy, preferably methoxy and ethoxy, particularly preferably methoxy, it is particularly preferred for all substituents $R^1$, $R^2$, $R^3$ and $R^4$ to be hydrogen.

The phthalic anhydrides II are known, such as phthalic anhydride, or can be obtained by known processes from benzoic acid derivatives (JOC, 51 (1986) 3439 to 3446; Synthesis (1985) 223 to 224).

The phthalides I are suitable, for example as starting materials for the synthesis of active ingredients for crop protection.

EXAMPLES

The catalysts used in the examples had the following compositions (data in % by weight):

| Catalyst | Composition |
| --- | --- |
| A | 98% of CoO; 0.1% of $Na_2O$ |
| B | 25% of NiO; 5% of $ZrO_2$; 70% of $SiO_2$ |
| C | 50% of NiO; 50% of $Cr_2O_3$ |
| D | 0.5% of PdO; 94.5% of $Al_2O_3$; 5% of $PrO_2$ |
| E | 5% of AgO; 0.4% of PdO; 1.4% of $MnO_2$; 93% of $Al_2O_3$ |
| F | 1% of Ru; 1.2% of Sn; 1.3% of B; 96.5% of $Al_2O_3$ |
| G | 52% of CuO; 48% of $Al_2O_3$ |
| H | 3% of Pd; 3% of Re; 94% of carbon |
| I | 64% of CoO; 18% of CuO; 7% of $MnO_2$; 4% of MoO; 9.2% of $Na_2O$ |
| K | 50% of NiO; 30% of $ZrO_2$; 18% of CuO; 1.5% of $MoO_2$; 0.2% of $Na_2O$ |

EXAMPLE 1

The hydrogenation was carried out in a 300 ml stirred autoclave containing 5 g of catalyst A, 50 g of phthalic anhydride and 50 ml of tetrahydrofuran. The mixture was hydrogenated for 12 hours at 200° C. and an overall pressure of 260 bar.

Analysis of the liquid reaction product by gas chromatography gave a yield of phthalide of 84%. 7.5% of phthalic anhydride were also found.

EXAMPLES 2 TO 10

Hydrogenation was carried out by methods similar to that in Example 1. The catalysts and reaction conditions used in each case are shown in Table 1 together with the composition of phthalic anhydride and phthalide.

TABLE 1

| Catalyst | Temperature [°C.] | Phthalic anhydride [GC area %] | Phthalide [GC area %] |
| --- | --- | --- | --- |
| B | 250 | — | 71 |
| C | 250 | 15 | 72 |
| D | 250 | — | 86 |
| E | 250 | — | 89 |
| F | 250 | 5.5 | 80 |
| G | 200 | 44 | 51 |
| H | 200 | 27 | 59 |
| I | 200 | 37 | 14 |
| K | 150 | 8.3 | 58 |

EXAMPLE 11

The hydrogenation was carried out in a tubular reactor (length 2000 mm, diameter 16 mm) containing catalyst D in a fixed bed. The reactor was heated to the reaction temperature via an external heating mantle containing oil. The gaseous and liquid starting materials were fed through the reactor from top to bottom. The hydrogenation product was decompressed and separated into its gaseous and liquid constituents in a gas/liquid separator.

The catalyst was employed in the form of grit with a particle size of 2 to 4 mm and was activated by means of hydrogen before the hydrogenation was commenced.

0.25 kg/h of phthalic anhydride per liter of catalyst in the form of a 10% strength solution in tetrahydrofuran and 0.5 m$^3$/h of hydrogen per kg of catalyst were fed to the reactor at 230° C. and at an overall pressure of 300 bar.

Analysis of the liquid reaction product by gas chromatography gave a conversion of 84% and a selectivity of 88%.

EXAMPLES 12 AND 13

The hydrogenations were carried out by methods similar to that of Example 11. The catalysts and the reaction conditions used in each case are shown in Table 2 together with the conversion and selectivity.

TABLE 2

| Catalyst | Weight hourly space velocity [kg/l × h] | Temp. [°C.] | Conversion [GC area %] | Selectivity [GC area %] |
| --- | --- | --- | --- | --- |
| E | 0.12 | 240 | 96 | 89 |
| I | 0.06 | 170 | 86 | 64 |

EXAMPLES 14 TO 17

The hydrogenations were carried out by methods similar to that of Example 11, but using a reactor having a length of 2000 mm and a diameter of 45 mm.

The catalysts and reaction conditions used in each case are shown in Table 3 together with the conversion and selectivity.

TABLE 3

| Catalyst | Weight hourly space velocity [kg/1 × h] | Temp. [°C.] | Conversion [GC area %] | Selectivity [GC area %] |
|---|---|---|---|---|
| H | 0.06 | 180 | 93 | 95 |
| F | 0.12 | 240 | 83 | 52 |
| G | 0.25 | 210 | 68 | 96 |
| K | 0.04 | 100 | 72 | 72 |

We claim:

1. A process for the preparation of phthalides of the formula

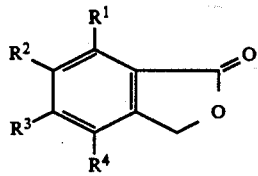

I where R1, R2, R3 and R4, independently of one another, are hydrogen C1-C4 alkyl or C1-C3 alkoxy, which comprises: reacting a phthalic anhydride of the formula

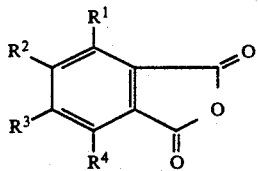

II where R1, R2, R3 and R4 are as defined above with hydrogen in the presence of a hydrogenation catalyst at from 50° to 400° C. and at from 1 to 400 bar, wherein the hydrogenation catalyst employed is a fixed-bed catalyst essentially free from Lewis acids and is selected form the group consisting of:
  a) oxides of the elements of main groups one to four of the Periodic Table of Elements, oxides of the elements of sub-groups one to eight of the Periodic Table of Elements, oxides of the elements of the lanthanide group, or mixtures of said oxides; and
  b) metallic catalysts wherein the metal is selected from the group consisting of ruthenium, rhenium, palladium, platinum, boron, tin and mixtures thereof on support materials.

2. A process for the preparation of phthalides of the formula I as claimed in claim 1, wherein the reaction is carried out at from 150° to 250° C.

3. A process for the preparation of phthalides of the formula I as claimed in claim 1, wherein the reaction is carried out at from 50 to 400 bar.

4. A process as claimed in claim 1, wherein the reaction is carried out at from 100 to 300 bar.

5. A process as claimed in claim 1, where the phthalic anhydride II dissolved in an inert solvent is passed through the fixed-bed of said hydrogenation catalyst.

6. A process as claimed in claim 1, wherein the oxide catalyst consists essentially of CoO.

7. A process as claimed in claim 1, wherein the catalyst consists essentially of a mixture of the oxides NiO, ZrO and SiO$_2$.

8. A process as claimed in claim 1, wherein the oxide catalyst consists essentially of a mixture of the oxides NiO and Cr$_2$O$_3$.

9. A process as claimed in claim 1, wherein the oxide catalyst consists essentially of a mixture of the oxides PdO, Al$_2$O$_3$ and PrO$_2$.

10. A process as claimed in claim 1, wherein the metallic catalyst consists essentially of a mixture of the metals Ru, Sn and B on Al$_2$O$_3$ as a support material.

11. A process as claimed in claim 1, wherein the oxide catalyst consists essentially of an oxide of the elements of subgroups one and eight of the Periodic Table, aluminum, boron, titanium, zirconium, praseodymium, tin, silicon, manganese and mixtures thereof.

12. A process as claimed in claim 1, wherein the oxide catalyst consists essentially of an oxide of the elements of subgroups one and eight of the Periodic Table, aluminum, silicon, titanium, zirconium, praseodymium, manganese and mixtures thereof.

13. A process as claimed in claim 1, wherein the metallic catalyst on a support consists essentially of a metal selected from the group consisting of ruthenium, rhenium, palladium, platinum, boron, tin and mixtures thereof on a support material selected from the group consisting of pumice, silicon dioxide, aluminum oxide, titanium dioxide, activated charcoal, silicates and zeolites.

14. A process as claimed in claim 13, wherein the metallic catalyst consists essentially of a metal selected from the group consisting of palladium, ruthenium and mixtures thereof on a support material selected from the group consisting of silicon dioxide, aluminum dioxide and activated charcoal.

15. A process as claimed in claim 14, wherein the metallic catalyst consists essentially of a mixture of palladium and rhenium on activated charcoal as a support material.

16. A process as claimed in claim 1, wherein the oxide catalyst consists essentially of a mixture of AgO, PdO, MnO and Al2O8.

* * * * *